US011352614B2

(12) United States Patent
Sebastian et al.

(10) Patent No.: US 11,352,614 B2
(45) Date of Patent: Jun. 7, 2022

(54) RUBISCO PROTEIN FIBERS

(71) Applicant: R.J. Reynolds Tobacco Company, Winston-Salem, NC (US)

(72) Inventors: Andries Sebastian, Winston-Salem, NC (US); John P. Mua, Advance, NC (US); David Neil McClanahan, Winston-Salem, NC (US); Sammy Eni Eni, Winston-Salem, NC (US); Thaddeus J. Jackson, High Point, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 16/936,221

(22) Filed: Jul. 22, 2020

(65) Prior Publication Data

US 2020/0347376 A1 Nov. 5, 2020

Related U.S. Application Data

(62) Division of application No. 15/622,994, filed on Jun. 14, 2017, now Pat. No. 10,745,682.

(51) Int. Cl.
| | |
|---|---|
| *C12N 9/88* | (2006.01) |
| *A23J 1/00* | (2006.01) |
| *A24B 15/24* | (2006.01) |
| *A24B 15/12* | (2006.01) |
| *A23J 3/26* | (2006.01) |
| *A23J 3/34* | (2006.01) |
| *A24B 15/16* | (2020.01) |
| *A23J 3/14* | (2006.01) |

(52) U.S. Cl.
CPC ............. *C12N 9/88* (2013.01); *A23J 1/007* (2013.01); *A23J 3/14* (2013.01); *A23J 3/26* (2013.01); *A23J 3/34* (2013.01); *A24B 15/12* (2013.01); *A24B 15/16* (2013.01); *A24B 15/24* (2013.01); *A24B 15/241* (2013.01); *C12Y 401/01039* (2013.01)

(58) Field of Classification Search
None
See application file for complete search history.

(56) References Cited

U.S. PATENT DOCUMENTS

| | | |
|---|---|---|
| 2,098,836 A | 11/1937 | Ressler |
| 2,232,662 A | 2/1941 | Hockenyos |
| 3,684,520 A | 8/1972 | Bickoff et al. |
| 3,823,128 A | 7/1974 | Bickoff et al. |
| 3,959,246 A | 5/1976 | Bickoff et al. |
| 4,268,632 A | 5/1981 | Wildman et al. |
| 4,289,147 A | 9/1981 | Wildman et al. |
| 4,333,871 A | 6/1982 | De Jong |
| 4,338,340 A | 7/1982 | Morimoto ............... A23J 3/26 426/104 |
| 4,340,676 A | 7/1982 | Bourque |
| 4,347,324 A | 8/1982 | Wildman et al. |
| 4,400,471 A | 8/1983 | Johal |
| 4,588,691 A | 5/1986 | Johal |
| 4,941,484 A | 7/1990 | Clapp et al. |
| 6,033,895 A | 3/2000 | Garger et al. |
| 7,337,782 B2 | 3/2008 | Thompson |
| 7,503,330 B2 | 3/2009 | Borschke et al. |
| 7,726,320 B2 | 6/2010 | Robinson et al. |
| 9,175,052 B2 | 11/2015 | Gerardi et al. |
| 9,301,544 B2 | 4/2016 | Mua et al. |
| 9,485,953 B2 | 11/2016 | Moldoveanu et al. |
| 2009/0025739 A1 | 1/2009 | Brinkley et al. |
| 2010/0093054 A1 | 4/2010 | Lo et al. |
| 2011/0174323 A1 | 7/2011 | Coleman, III et al. |
| 2011/0287681 A1 | 11/2011 | DeVall |
| 2012/0192880 A1 | 8/2012 | Dube et al. |
| 2012/0260929 A1 | 10/2012 | Coleman et al. |
| 2012/0272976 A1 | 11/2012 | Byrd et al. |
| 2013/0072661 A1 | 3/2013 | Kale |
| 2013/0256942 A1 | 10/2013 | Domaske |
| 2013/0269719 A1 | 10/2013 | Marshall et al. |
| 2014/0096780 A1 | 4/2014 | Gerardi |
| 2014/0261495 A1 | 9/2014 | Novak, III et al. |

(Continued)

FOREIGN PATENT DOCUMENTS

| | | |
|---|---|---|
| EP | 1067946 | 1/2001 |
| EP | 1691759 | 8/2006 |

(Continued)

OTHER PUBLICATIONS

Makino et al. Plant and Cell Physiology (1983), 24(6),1169-73 (Year: 1983).
Barbeau et al.; Ribulose Bisphosphate Carboxy Lase-Oxygenase Rubisco from Green Leaves Potential as a Food Protein; vol. 4, No. 1; USA, dated Jan. 1, 1988.
European Patent Office; International Search Report and Written Opinion of Application Serial No. PCT/US2018/037367; 14 pages; dated Sep. 21, 2018.

(Continued)

*Primary Examiner* — Christian L Fronda

(74) *Attorney, Agent, or Firm* — Womble Bond Dickinson (US) LLP

(57) ABSTRACT

Ribulose-1,5-bisphosphate oxygenase (RuBisCO) protein fibers and a method of producing them are disclosed herein. The method of producing one or more RuBisCO protein fibers including obtaining RuBisCO, for example from tobacco, combining the RuBisCO with one or more plasticizers, heating the combination of the RuBisCO and the one or more plasticizers up to about 140 degrees C., filtering the heated combination through an about 20 μm filter, and passing the filtered combination through an orifice to produce one or more RuBisCO protein fibers.

20 Claims, 2 Drawing Sheets

(56) References Cited

U.S. PATENT DOCUMENTS

| | | | |
|---|---|---|---|
| 2014/0271952 A1 | 9/2014 | Mua | A24B 15/241 424/751 |
| 2014/0343254 A1 | 11/2014 | Gerardi et al. | |
| 2016/0029663 A1 | 2/2016 | Gerardi et al. | |
| 2016/0192697 A1 | 7/2016 | Mua et al. | |

FOREIGN PATENT DOCUMENTS

| | | | |
|---|---|---|---|
| EP | 2403888 | 1/2012 | |
| WO | 2008143914 | 11/2008 | |
| WO | 2011078671 | 6/2011 | |
| WO | 2013010042 | 1/2013 | |
| WO | WO-2013093921 A * | 6/2013 | ............. A61L 27/34 |
| WO | WO-2016040754 A1 * | 3/2016 | ............. A24F 23/02 |

OTHER PUBLICATIONS

Davis et al.; Tobacco Production, Chemistry and Technology—Leaf Chemistry—Basic Chemical Constituents of Tobacco Leaf and Differences among Tobacco Types, 20 Pages; dated 1999.

\* cited by examiner

RUBISCO PROTEIN FIBERS

CROSS-REFERENCE TO RELATED APPLICATIONS

The present application is a divisional of U.S. application Ser. No. 15/622,994 filed Jun. 14, 2017, which is incorporated by reference herein in its entirety.

BACKGROUND

Numerous uses of tobacco and tobacco-based products have been proposed. For example, tobacco has been smoked in pipes, cigarettes, and cigars. See e.g. Tobacco Production, Chemistry and Technology, Davis et al. (Eds.) p. 346 (1999). More recently, there has been focus on various ways of providing various sensations of smoking, without delivering to a smoker quantities of incomplete combustion and pyrolysis products that may result from the burning of tobacco. See e.g., the background art set forth in U.S. Pat. No. 7,503,330 to Borschke et al. and U.S. Pat. No. 7,726,320 to Robinson et al., U.S. Pat. Pub. No. 2014/0261495 to Novak, III et al., and U.S. Pat. Pub. No. 2014/0096780 to Gerardi. In addition to smoking, tobacco may also be used in so-called smokeless forms. See e.g. the background art set forth in U.S. Pat. Pub. 2012/0272976 to Byrd et al. Furthermore, various materials derived and/or extracted from tobacco have been proposed to have uses in certain industrial applications. See e.g. U.S. Pat. No. 2,098,836 to Ressler; U.S. Pat. No. 2,232,662 to Hockenyos, U.S. Pat. No. 4,347,324 to Wildman et al., U.S. Pat. No. 4,289,147 to Wildman et al., U.S. Pat. Pub. Nos. 2011/01287681 to DeVall, and 2012/0260929 to Coleman et al.

Methods of extracting proteins from tobacco and tobacco components have been proposed in U.S. Pat. No. 9,301,544 to Mua et al., U.S. Pat. No. 9,175,052 to Gerardi et al., U.S. Pat. Pub. No. 2016/0192697 to Mua et al., and U.S. Pat. Pub. No. 2016/0029663 to Gerardi et al. It may be desirable to utilize protein compositions extracted from tobacco for various purposes, including the production of protein fibers. Generally, natural protein fibers (e.g. wool, silk, and the like) are well known in the textile industry. However, these animal fibers may not be abundant and may be more expensive than protein fibers from other sources. Synthetic protein fibers that are derived from soy cake and milk have been proposed, but these sources are also traditional food sources. It may be desirable to utilize other, non-food, sources for the production of protein fibers.

Ribulose-1,5-bisphosphate carboxylase/oxygenase (hereinafter "RuBisCO") is considered the most abundant plant protein known, as it is an enzyme involved in the first major step carbon fixation by plants and other photosynthetic organisms, making it an abundant, potentially non-food protein source that may be desirable in the production of protein fibers. For example, RuBisCO may comprise up to about 25% of the total protein content of a leaf and up to about 10% of the solid matter of a leaf. Furthermore, tobacco plants may have the highest potential yield per acre of RuBisCO of all plants, without the limitation of also being a traditional food source.

SUMMARY

The present disclosure is directed to inventive ribulose-1,5-bisphosphate oxygenase protein fibers and methods of producing them. In one aspect a method includes: obtaining ribulose-1,5-bisphosphate oxygenase protein; combining the ribulose-1,5-bisphosphate oxygenase protein with one or more plasticizers; heating the ribulose-1,5-bisphosphate oxygenase combined with the one or more plasticizers to up to about 140 degrees C. and forming a mixture; filtering the mixture through an about 20 μm filter; and, passing the mixture through an orifice to produce the one or more ribulose-1,5-bisphosphate oxygenase protein fibers.

In some embodiments the ribulose-1,5-bisphosphate oxygenase protein may be obtained from one or more tobacco plants. In other embodiments, the method may further comprise purifying the obtained ribulose-1,5-bisphosphate oxygenase protein. In still other embodiments the method may further comprise combining the obtained ribulose-1,5-bisphosphate oxygenase protein with one or more additional proteins.

In some embodiments, the one or more plasticizers may be selected from a group consisting of: water, aqueous polysaccharide solutions, alcohols, polyalcohols, glycerol (glycerine), gum Arabic, and aqueous solutions of carbohydrates. In other embodiments, the method further may comprise adding one or more additional additives selected from a group consisting of: one or more crosslinking agents, one or more glossing agents, and wax. Instill other embodiments, the one or more crosslinking agents may be selected from a group of calcium chloride, calcium phosphate, calcium sulfate, dialdehyde starch, formaldehyde, glutaraldehyde, dimethyl adipimidate, and dimethyl suberimidate. In some embodiments, the method further may comprise surface treating the one or more ribulose-1,5-bisphosphate oxygenase protein fibers.

In another aspect a method of producing one or more ribulose-1,5-bisphosphate oxygenase protein fibers includes: extracting ribulose-1,5-bisphosphate oxygenase protein from tobacco; feeding the extracted ribulose-1,5-bisphosphate oxygenase protein into an extruder; adding one or more plasticizers to the extruder forming a ribulose-1,5-bisphosphate oxygenase protein mixture; moving the ribulose-1,5-bisphosphate oxygenase protein mixture through one or more barrels of the extruder; heating the ribulose-1,5-bisphosphate oxygenase protein mixture to up to about 140 degrees C.; filtering the ribulose-1,5-bisphosphate oxygenase protein mixture with an about 20 μm filter; and exiting the ribulose-1,5-bisphosphate oxygenase protein mixture through an orifice of the extruder to shape the mixture as it exits the extruder forming one or more ribulose-1,5-bisphosphate oxygenase protein fibers.

In some embodiments, the extracted ribulose-1,5-bisphosphate oxygenase protein may be in a dry powder form. In other embodiments, the method may further comprise purifying the extracted ribulose-1,5-bisphosphate oxygenase protein. Instill other embodiments, the method may further comprise obtaining additional dry material; combining the additional dry material with the extracted ribulose-1,5-bisphosphate oxygenase protein to form a mixture; and feeding the mixture of the additional dry material and the extracted ribulose-1,5-bisphosphate oxygenase protein into the extruder. In some embodiments, the additional dry material may include one or more additional proteins. In other embodiments, the additional dry materials may include one or more additional additives selected from a group consisting of: one or more crosslinking agents, one or more glossing agents, and wax. In still other embodiments, the one or more crosslinking agents may be selected from a group of calcium chloride, calcium phosphate, calcium sulfate, dialdehyde starch, formaldehyde, glutaraldehyde, dimethyl adipimidate, and dimethyl suberimidate. In some embodiments, the one or more plasticizers may be selected from a group consisting of: water, aqueous polysaccharide solutions, alcohols, polyalcohols, glycerol (glycerine), gum Arabic, and aqueous solutions of carbohydrates. In other embodiments, the method further may comprise surface treating the one or more ribulose-1,5-bisphosphate oxygenase protein fibers.

In still another aspect, one or more ribulose-1,5-bisphosphate oxygenase protein fibers may be produced by a process comprising the steps of: extracting ribulose-1,5-bisphosphate oxygenase protein from tobacco; feeding the extracted ribulose-1,5-bisphosphate oxygenase protein into an extruder; adding a plasticizer to the extruder forming a ribulose-1,5-bisphosphate oxygenase protein mixture; moving the ribulose-1,5-bisphosphate oxygenase protein mixture through one or more barrels of the extruder; heating the ribulose-1,5-bisphosphate oxygenase protein mixture to up to about 140 degrees C.; filtering the ribulose-1,5-bisphosphate oxygenase protein mixture with an about 20 μm filter, and exiting the ribulose-1,5-bisphosphate oxygenase protein mixture through an orifice to shape the mixture as it exits the extruder forming the one or more ribulose-1,5-bisphosphate oxygenase protein fibers.

In some embodiments, the one or more ribulose-1,5-bisphosphate oxygenase protein fibers may be formed into a fabric selected from a group consisting of: woven fabric, non-woven fabric, knitted fabric, and/or a combination thereof. In other embodiments, the one or more ribulose-1,5-bisphosphate oxygenase protein fibers may be incorporated into a biomedical device. In still other embodiments, the one or more ribulose-1,5-bisphosphate oxygenase protein fibers may be used to form one or more food-grade pouches. In some embodiments, the one or more ribulose-1,5-bisphosphate oxygenase protein fibers may be used to form one or more tobacco pouches.

DETAILED DESCRIPTION

Figure 1:
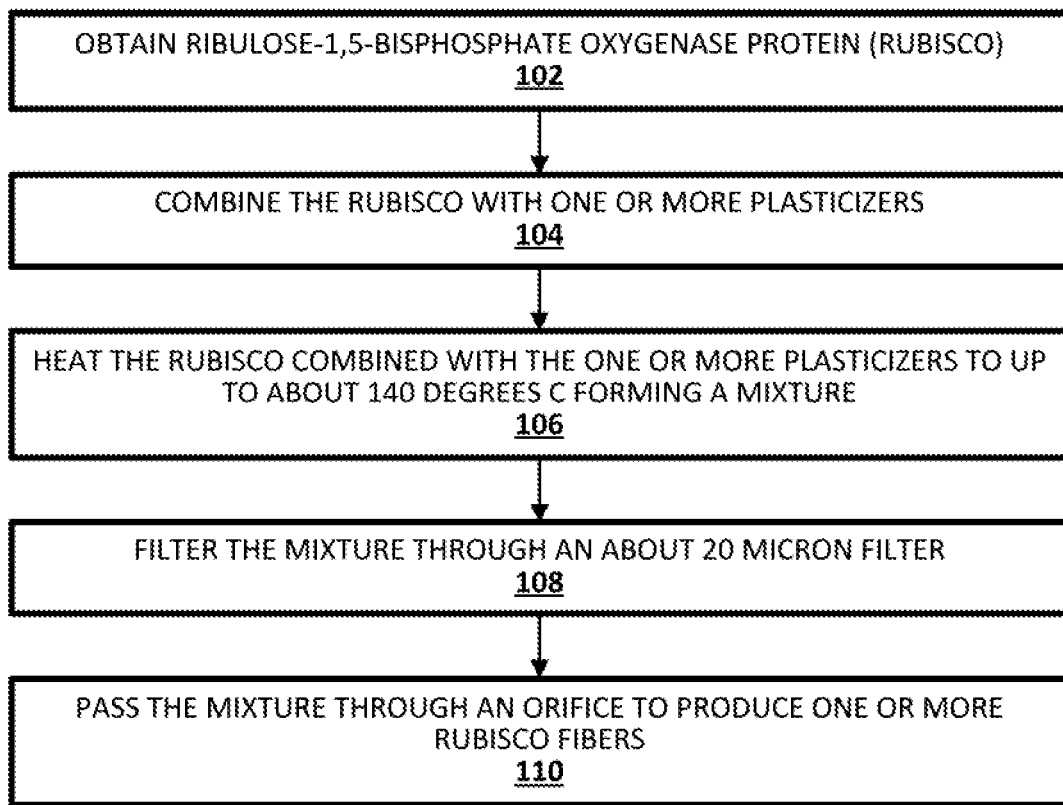
FIG. 1 illustrates an exemplary embodiment of a method of producing RuBisCO fibers.

Generally, the present invention provides methods for generating protein fibers utilizing ribulose-1,5-bisphosphate carboxylase-oxygenase (hereinafter "RuBisCO"), whose subunit molecular weight is about 550 kD. Furthermore, when subjected to heating and other processing, particularly in an aqueous slurry, RuBisCO is known to exhibit various functional properties that may be desirable in a protein source for fiber formation, including solubility, viscosity builder, gel formation, water retention, foaming, and emulsifying attributes. As discussed previously, RuBisCO is considered the most abundant plant protein known, as it is present in every plant that undergoes photosynthesis. RuBisCO may comprise up to about 25% of the total protein content of a leaf and up to about 10% of the solid matter of a leaf. In particular, in one embodiment, the RuBisCO proteins utilized in the formation of such fibers may be extracted from one or more plants of the *Nicotiana* species (generally referred to herein as "tobacco"), which may have among the highest potential yield per acre of RuBisCO of all plants. Furthermore, the use of plant protein in the production of protein fibers, in particular the use of a non-food plant source (e.g. tobacco) may be a more sustainable and environmentally friendly source compared to other sources including, for example protein sourced from animals.

Although the present disclosure focuses primarily on RuBisCO protein extracted from a plant of the *Nicotiana* species, it is to be understood that various methods disclosed herein may be applicable to RuBisCO extracted from sources other than tobacco. In some embodiments, RuBisCO proteins may be extracted from any photosynthesizing plant. In other embodiments, RuBisCO proteins may be extracted from other photosynthesizing organisms, including, but not limited to, various species of photosynthetic bacteria.

The plant of the *Nicotiana* species may be employed in either an immature or mature form, and may be used in either a green form or a cured form, as described in U.S. Patent Publication No. 2012/0192880 to Dube et al., which is incorporated by reference herein. The tobacco material may be subjected to various treatment processes such as, refrigeration, freezing, drying (e.g., freeze-drying or spray-drying), irradiation, yellowing, heating, cooking (e.g., roasting, frying or boiling), fermentation, bleaching, or otherwise subjected to storage or treatment for later use. In some embodiments, harvested tobacco can be sprayed with a buffer or antioxidant (e.g., a sodium met-abisulfite buffer) to prevent the green plants from browning prior to extract and purification treatments. Other exemplary processing techniques are described, for example, in U.S. Patent Publication Nos. 2009/0025739 to Brinkley et al. and 2011/0174323 to Coleman, III et al., which are incorporated by reference herein. Additionally, at least a portion of the plant of the *Nicotiana* species may be treated with enzymes and/or probiotics before or after harvest, as discussed in U.S. Pat. Pub. No. 2013/0269719 to Marshall et al. and U.S. Pat. No. 9,485,953 to Moldoveanu, which are incorporated herein by reference.

Generally, any method known in the art may be used for the extraction of RuBisCO. Including, but not limited to those methods described in U.S. Pat. No. 9,301,544 to Mua et al., U.S. Pat. No. 9,175,052 to Gerardi et al., U.S. Pat. Pub. No. 2016/0192697 to Mua et al., and U.S. Pat. Pub. No. 2016/0029663 to Gerardi et al., all of which are incorporated by reference herein in their entireties. Other exemplary methods for extracting proteins, such as RuBisCO, from tobacco and other plants include, but are not limited to, those described in U.S. Pat. No. 7,337,782 to Thompson; U.S. Pat. No. 6,033,895 to Garger et al.; U.S. Pat. No. 4,941,484 to Clapp et al.; U.S. Pat. Nos. 4,588,691 and 4,400,471 to Johal; U.S. Pat. No. 4,347,324 to Kwanyuen et al., U.S. Pat. No. 4,340,676 to Bourque; U.S. Pat. No. 4,333,871 to DeJong; U.S. Pat. Nos. 4,289,147 and 4,268,632 to Wildman et al.; U.S. Pat. Nos. 3,959,246, 3,823,128, and 3,684,520 to Bick-off et al.; U.S. Pat. Pub. Nos. 2010/0093054 to Lo et al. and 2013/0072661 to Kale; U.S. Pat. No. 9,301,544 to Mua et al.; Int'l Appl. Publ. Nos. WO2011/078671 to Van de Velde et al. and WO2008/143914 to Lo; and EP Pat. Publ. Nos. EP 2403888 to Parker et al.; EP 1691759 to Boddupalli et al.; and EP 1067946 to Brinkhaus et al., which are all incorporated by reference herein in their entireties.

Generally, an example embodiment of the extraction process includes creating what is commonly referred to in the industry as "green juice" by extracting a whole plant, for example a tobacco plant, with a buffer solution. This "green juice" may be subjected to centrifugation in order to remove debris. Supernatant collected from this centrifugation may then be filtered. First, tangential flow filtration with a filter size of about 0.1 microns may be used to collect a first faction containing RuBisCO. A second filtration system with a filter size of about 10 kDA may then be used to collect a second faction, for example the F2 protein faction, which is a mixture of soluble proteins of cytoplasmic and chloroplastic origin. F2 proteins and peptides generally have molecular weights ranging from about 3 kD to about 100 kD. This general process may result in the production of pellets or other non-liquid product (e.g. powder) that contain various starches and proteins, including RuBisCO, and a liquid extract and distillate that may contain nicotine. These pellets and other non-liquid products (e.g. powder) may be used in the production of fibers, and/or they may be used in various other downstream processing. In some embodiments, the liquid extract and distillate may be discarded.

In some embodiments, the extracted RuBisCO proteins may be, optionally, further processed in order to improve the purity of the protein sample. In some embodiments, the RuBisCO utilized in fiber production may be about 70% to about 80% pure. In other embodiments, the extracted RuBisCO may undergo further processing in order to concentrate the extracted proteins. In some embodiments, further processing may include adjusting the pH, heating and/or stirring of RuBisCO slurry, retentate, or concentrate so as to in order to re-solubilize the protein. In other embodiments, the concentrate may be also be filtered. In still other embodiments, the RuBisCO retentate may be spray or freeze dried into a powder.

Additionally, the extracted RuBisCO proteins may also be, optionally, combined with other proteins. This combination may occur either before or after the additional processing previously described. In some instances these other proteins may be derived from the same source as the RuBisCO, for example one or more tobacco plants. In some embodiments, these other proteins may be contained in the previously described F2 faction of the extraction. In other instances the other protein may be derived from a separate plant source, an animal source, or any other source of proteins known in the art.

The RuBisCO proteins and, if used, any optional additional proteins may be combined with a plasticizer in order to be plasticized. In some embodiments, the RuBisCO and optional additional proteins may be in a dry form (e.g. powdered, pelletized, or the like). In other embodiments, RuBisCO and optional additional proteins may be in liquid form or in a liquid solution. Generally, plasticizers are low molecular weight, non-volatile compounds used as additives or incorporated into other material in order to increase flexibility and dispensability. The process of plasticizing a protein-based polymer or fiber may be affected by the selected plasticizer's molecular weight, as well as the number and position of various hydroxyl groups. Various plasticizers known in the art may be selected including, but not limited to, water, aqueous polysaccharide solutions, alcohols, polyalcohols, glycerol (glycerine), gum Arabic, aqueous solutions of carbohydrates, or any combinations thereof. The amount of plasticizer added may vary depending on the amount of protein, for example between about 0.01% and 10% of the amount of protein. Depending on the plasticizer used, the moisture content of the RuBisCO protein may require adjustment. In some embodiments the moisture content may range from about 15% to about 30%. In other embodiments, the moisture content may range from about 15% to about 20%.

One or more other additives may also be included in the protein/plasticizer mixture, such as, for example, glossing agents or crosslinking agents. The amounts of each additive, where used, may vary dependent on the amount of protein. For example, the amount of glossing agent may range from about 0.1% to about 3% of the amount of protein. Generally, a crosslinking agent bonds one polymer with another. A crosslinking agent may be used to promote certain desirable changes in a resulting fiber's physical properties. Such changes in physical properties may include, but are not limited to, causing a polymer to harden, have an increased melting temperature, and/or the like. Crosslinks may also be formed by chemical reactions under heat, pressure, pH changes, or the like. Examples of possible crosslinking agents may include, but are not limited to, various calcium salts (e.g. calcium chloride, calcium phosphate, calcium sulfate, etc.), various polysaccharides (e.g. dialdehyde starch), formaldehyde, glutaraldehyde, dimethyl adipimidate, dimethyl suberimidate, glyoxal, maleic anhydride, or any other crosslinking agents known in the art.

In some embodiments, wax may also be added to the mixture in order to provide additional stability to the resulting fiber. In some embodiments, added waxes may include naturally-derived waxes, such as beeswax, lanolin carnauba wax canelilla wax, or ouricury wax. In other embodiments, added wax may include petroleum-derived waxes, such as paraffin. In still other embodiments, added wax may include any combination of naturally-derived wax, modified natural wax, or petroleum-derived wax.

The RuBisCO protein, and any addition proteins if used, may be plasticized with a plasticizer. The plasticizer may be selected may any of those described herein, or may be any plasticizer known in the art. In some embodiments, the plasticizer may an aqueous solution and/or glycerol. The RuBisCO protein (and additional proteins, if used), in combination with the plasticizer, may be exposed to heat and thermally plasticized. The plasticizing process may require mechanical mixing. In some embodiments, this mechanical mixing may be in the form of stirring. In other embodiments, this mechanical mixing may be in the form of kneading or pumping. In some embodiments, the source of the heat may be external, such as for example some type of heating element, hot plate, flame, or the like. In other embodiments, the source of the heat may be internal, for example heat generated by the mechanical mixing. The heating may cause all components to melt, and in some embodiments the temperature may reach as high as 140 degrees C. during the plasticization process. In other embodiments, the temperature may range from about 80 degrees C. to about 100 degrees C. during the plasticization process.

FIG. 1 illustrates an exemplary embodiment of a process for generating RuBisCO fibers 100. At block 102, RuBisCO protein is obtained. In some embodiments, the RuBisCO obtained is in dry form, for example a powder. At block 104, the RuBisCO is combined with one or more plasticizers to form a mixture. The plasticizer used may be any known in the art, including, but not limited to, water, aqueous polysaccharide solutions, alcohols, polyalcohols, glycerol (glycerine), gum Arabic, or aqueous solutions of carbohydrates. At block 106, the mixture of RuBisCO and plasticizer(s) is heated to a temperature of up to 140 degrees C. Heating may be any means known in art, including both direct and indirect methods of heating. At block 108, the mixture is passed through an about 20 μm filter. At block 110, the filtered mixture is passed through an orifice (e.g. a die, jet, or the like) to produce one or more RuBisCO fibers. The diameter of the resulting fiber may be dependent on the size of the opening of the orifice.

In some embodiments, a hot melt extruder may be used for the plasticization and processing of the RuBisCO protein (and, if used, additional proteins) into fibers. Industrial extruders have long been used in various industries for varying purposes. Generally, a hot melt extruder consists of a feeding hopper, one or more barrels, and at least one screw to move the mixture. The hot melt extruder may further include a heating element for the one or more barrels, one or more conveyor belts, a pump for delivering solvents, and/or monitoring equipment including, but not limited to temperature and pressure gauges, control panels, and the like. The process of hot melt extrusion may generally be described as: feeding the extruder various components through a hopper and/or through a solvent delivery pump; moving the mixture through the one or more barrels, which may also include heating the mixture; filtering the melted mixture; exiting the mixture through an orifice (or a die) that may be specifically designed to shape the mixture leaving the extruder; and, various optional downstream processing, such as cooling, cutting, collecting, and the like, of the fibers recently exited from the extruder.

Figure 2:
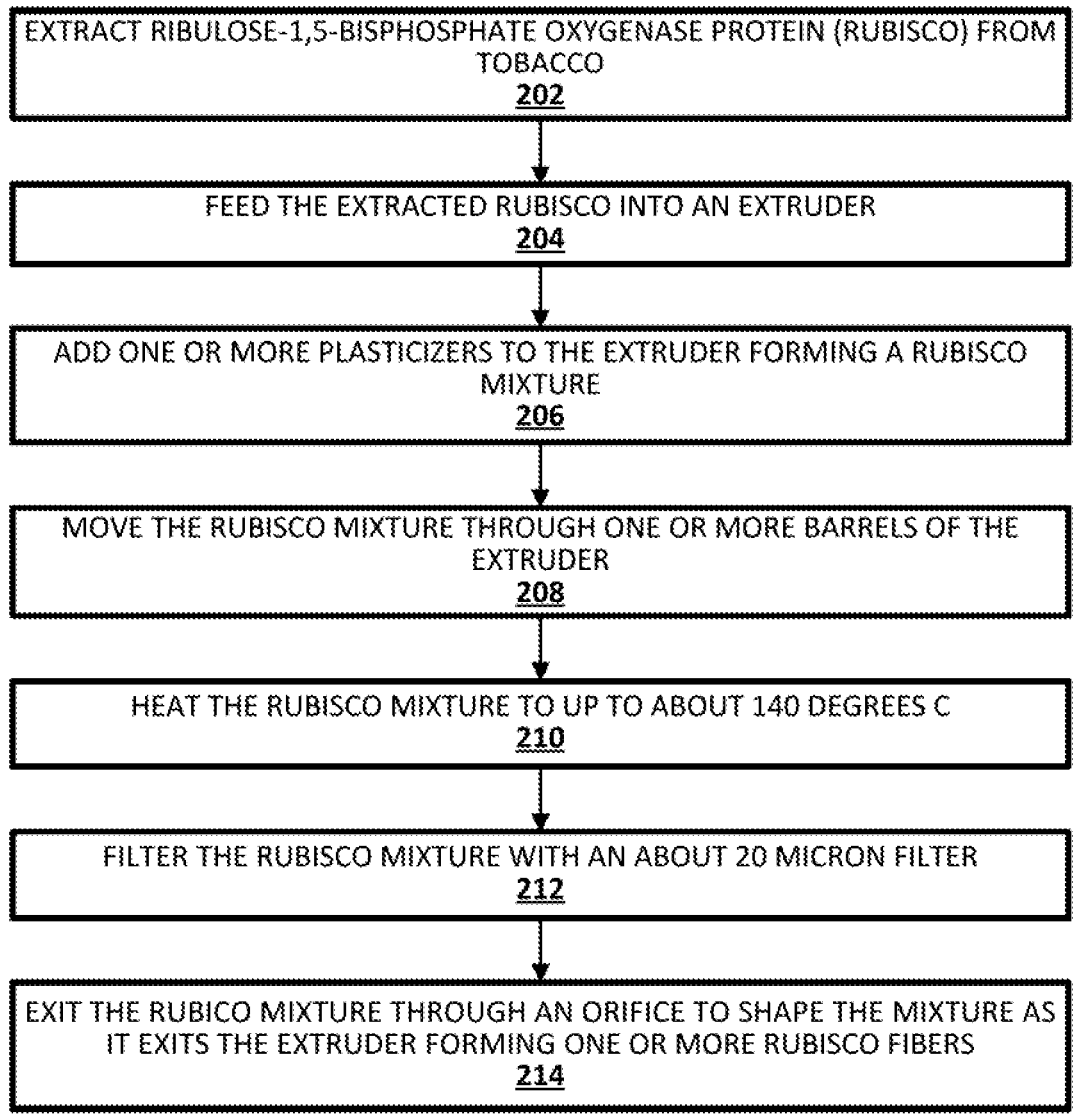
FIG. 2 illustrates another exemplary embodiment of a method of producing RuBisCO fibers.

FIG. 2 illustrates another exemplary process of forming RuBisCO fibers 200 that may include the use of a hot melt extruder. At block 202, RuBisCO is extracted from one or more tobacco plants. This extraction may be through any method of extraction known in the art, including those discussed previously. At block 204, the RuBisCO is fed into an extruder. In some embodiments, where the extracted RuBisCO protein is dry (for example in the form of a pellet or powder) the RuBisCO protein, and if used any additional protein(s), may be fed into the extruder through a hopper. Other dry components may also be fed into the extruder via a hopper as well. In some embodiments, all dry ingredients are mixed prior to begin fed into the extruder. Alternatively, in embodiments where the RuBisCO protein is a liquid or in a liquid solution, the RuBisCO protein and, if used, any additional protein(s), may be fed into the extruder through a solvent delivery pump. In some embodiments, all liquid ingredients are mixed prior to entering the extruder. In some embodiments, the dry and liquid components may enter at the same entry point, for example where the hopper and solvent delivery pump are in a single physical structure. In still other embodiments, the liquid ingredients may enter the extruder further downstream, in a different "zone" of the barrel.

At block 206, one or more plasticizers may be added to the extruder forming a mixture of plasticizer(s) and RuBisCO. Once the RuBisCO, plasticizer, and other optional components, if used, have entered the extruder, they may be, as shown at block 208, conveyed through one or more barrels, where they may be mechanically mixed. At block 210, the mixture may be heated to a desired temperature, for example up to 140 degrees C. In some embodiments, the one or more barrels may comprise heating elements; in other embodiments, the heat necessary may be produced as a by-product of the action of mechanical mixing. The plastification of the RuBisCO protein during the operation of the extruder may cause the components to be transformed into a rubber-like plastic state as a result of heating and/or mixing.

At block 212, the melted plasticized components may then be filtered to remove particulates. For example, the melted components may be passed through a 20 micron filter. At block 214, the filtered melted components may then be passed through an orifice (or die) of the extruder in order to shape the mixture. In some embodiments, this orifice may be a jet designed to create one or more fibers of a particular diameter, for example less than about 0.8 mm. After expulsion from the extruder, via the orifice, the mixture may cool and solidify into fibers. In some embodiments, the resulting fibers may be wound without any additional processing. In other embodiments, the fibers undergo one or more surface treatments prior to being wound. Examples of various surface treatments include various physical and/or chemical treatment methods, including but not limited to the application of any smoothing agents, waxes, lipophiles and/or crosslinking agents known in the art to the surface of the fiber. In still other embodiments, the fibers may be further processed prior to being wound. With respect to the process of winding the fibers, any winding technology known in the art may be used.

Further processing of the fibers may include twisting the fibers in order to form a yarn. In some embodiments, the resulting RuBisCO fibers may be twisted with other RuBisCO fibers. While in other embodiments, the resulting RuBisCO fibers may be twisted in combination with fibers from one or more other protein sources.

Further processing of the fibers may also include cutting the fibers to various desired lengths. For example, in some embodiments, it may be desirable to cut all of the fibers to the same length generating staple fiber. In other embodiments, it may be desirable to leave the fiber as one long, continuous fiber. Additional processing of the resulting RuBisCO fibers may also include, but is not limited to, bleaching the fibers, brightening the fibers, dying the fibers to a desirable color, and/or adding, for example through a treatment process, one or more flavors to the fiber.

Fibers resulting from the processes described herein may be suitable for various biomedical uses, industrial applications, and/or the like. Some examples of biomedical uses include, but are not limited to, using the resulting RuBisCO protein fibers in the engineering of tissue scaffolds, drug delivery devices, wound dressings, or the like. Some examples of industrial application using the resulting RuBisCO protein fibers includes, but is not limited to, the formation of fabrics. Such fabrics may be woven fabrics, non-woven fabrics, knitted fabrics, or a combination thereof. These fabrics may then be used for a variety of purposes such as for use the manufacturing of apparel, household items (e.g. towels, sheets, curtains, upholstery, and the like, and/or in industry (e.g. fillers, automobile upholstery, paper/tape, reinforcement, seatbelts, and the like). In some embodiments, the fibers may be used in an enclosure (e.g. a pouch) for tobacco, such as snus and/or moist tobacco. In other embodiments, the fibers may be used to form a food-grade enclosure, for example tea bags.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

EXAMPLES

The above described methods may be used for the formation of a variety of RuBisCO fibers. The following examples represent various RuBisCO fibers formed.

Example 1

RuBisCO protein was obtained and finely divided into powder (−100/+270 Tyler mesh). 14,475 g of powdered RuBisCO protein was measured, and 525 g of glycerin was added to the measured RuBisCO protein powder. The RuBisCO protein powder and glycerin were then thoroughly mixed using a model 300D Littleford horizontal plough dough mixer (Littleford Day, Inc. Florence, Ky.) for about 15 to about 20 minutes at about 150 rpm. The dry mixture was then commuted into the hopper of a model ZSK26 Coperion extruder (Werner and Pfeidderer, Ramsey, N.J.). The extruder barrel had a 30:1 length to diameter ratio, 26 inch internal diameter, and consisted of 10 heating zones or sections, plus a heated die component.

The extruder was set at a screw speed of about 45-65 rpm and the barrel sections and die operated at temperatures of about 100 to about 145 degree C. The die was cast with numerous about 0.1 to about 0.8 mm orifice/apertures similar to a "shower head." The extruder was fed at a rate of about 10.5 pounds per hour of dry formulation from a hopper, and 2.0 pounds per hour of water injected into the first heating zone. The formulation was extruded through the die, forming hair-like cylindrical fibers. The formulation spent approximately 55 to about 65 seconds in the extruder. The fibers were then cut as they exit the die and allowed to harden by ambient air drying for about 10 to about 20 minutes. The precise formulation used in Example 1 is shown in Table 1 below.

Example 2

Example 2 was prepared as described in Example 1, except that glycerin was replaced by propylene glycol as a humectant or plasticizer. The precise formulation used in Example 2 is shown in Table 1 below.

Example 3

Example 3 was prepared as described in Example 1, except that 5.5% of RuBisCO is substituted with the sodium alginate, a binder. Sodium alginate was utilized to improve fiber tensile strength. The precise formulation used in Example 3 is shown in Table 1 below.

Example 4

Example 4 was prepared as described in Example 3, except that calcium chloride, which is a crosslinking agent for alginate, was added to the formulation in order to further improve the tensile strength of the fibers.

TABLE 1

Formulations for RuBisCO Protein Fiber Extrusions of Examples 1-4.

| | Example 1 | | Example 2 | | Example 3 | | Example 4 | |
|---|---|---|---|---|---|---|---|---|
| | % dry weight | Weight (g)/batch | % dry weight | Weight (g)/batch | % dry weight | Weight (g)/batch | % dry weight | Weight (g)/batch |
| RuBisCO powder | 96.5 | 14,475.0 | 96.5 | 14,475.0 | 91.0 | 13,650.0 | 88.5 | 13,275.0 |
| Sodium alginate | | | | | 5.5 | 825.0 | 5.5 | 825.0 |
| Glycerin | 3.5 | 525.0 | | | 3.5 | 525.0 | 3.5 | 525.0 |
| Propylene glycol | | | 3.5 | 525.0 | | | | |
| Calcium chloride | | | | | | | 2.5 | 375.0 |
| Total | 100.0 | 15,000.0 | 100.0 | 15,000.0 | 100.0 | 15,000.0 | 100.0 | 15,000.0 |
| Water | | 3,000.0 | | 3,000.0 | | 3,000.0 | | 3,000.0 |

What is claimed is:

1. One or more tobacco-derived ribulose-1,5-bisphosphate oxygenase protein fibers containing substantially no components with a size above 20 μm, produced by a process comprising the steps of:
   extracting ribulose-1,5-bisphosphate oxygenase protein from tobacco;
   feeding the extracted ribulose-1,5-bisphosphate oxygenase protein into an extruder;
   adding a plasticizer to the extruder forming a ribulose-1,5-bisphosphate oxygenase protein mixture;
   moving the ribulose-1,5-bisphosphate oxygenase protein mixture through one or more barrels of the extruder;
   heating the ribulose-1,5-bisphosphate oxygenase protein mixture to up to about 140 degrees C.;
   exiting the ribulose-1,5-bisphosphate oxygenase protein mixture through an orifice to shape the mixture as it exits the extruder forming the one or more ribulose-1,5-bisphosphate oxygenase protein fibers.

2. The fibers of claim 1, wherein the one or more ribulose-1,5-bisphosphate oxygenase protein fibers are formed into a fabric selected from a group consisting of: woven fabric, non-woven fabric, knitted fabric, or a combination thereof.

3. The fibers of claim 1, wherein the one or more ribulose-1,5-bisphosphate oxygenase protein fibers are incorporated into a biomedical device.

4. The fibers of claim 1, where the one or more ribulose-1,5-bisphosphate oxygenase protein fibers are used to form one or more food-grade pouches.

5. The fibers of claim 1, where the one or more ribulose-1,5-bisphosphate oxygenase protein fibers are used to form one or more tobacco pouches.

6. The fibers of claim 1, further comprising a glossing agent, a crosslinking agent, a wax, or any combination thereof.

7. The fibers of claim 1, wherein the one or more ribulose-1,5-bisphosphate oxygenase protein fibers further comprise the plasticizer, and wherein the plasticizer is selected form the group consisting of water, aqueous polysaccharide solutions, alcohols, polyalcohols, glycerol, gum Arabic, aqueous carbohydrate solutions, and combinations thereof.

8. The fibers of claim 1, where a surface of the one or more ribulose-1,5-bisphosphate oxygenase protein fibers comprises a smoothing agent, wax, lipophile, crosslinking agent, or any combination thereof.

9. The fibers of claim 8, wherein the wax is selected from the group consisting of beeswax, lanolin carnuba wax, canelilla wax, ouricury wax, paraffin, and combinations thereof.

10. The fibers of claim 8, wherein the crosslinking agent is selected from the group consisting of a calcium salt, a polysaccharide, formaldehyde, glutaraldehyde, dimethyl adipimidate, dimethyl suberimidate, glyoxal, maleic anhydride, and combinations thereof.

11. The fibers of claim 1, further comprising one or more flavorants and/or colorants associated therewith.

12. The fibers of claim 1, further comprising one or more additional proteins.

13. The fibers of claim 12, wherein the one or more additional proteins are derived from a tobacco plant.

14. The fibers of claim 12, wherein the one or more additional proteins are derived from a plant source other than tobacco or an animal source.

15. The fibers of claim 1, further comprising sodium alginate.

16. The fibers of claim 15, further comprising calcium chloride.

17. A yarn comprising two or more of the fibers of claim 1, twisted around one another.

18. The fibers of claim 1, in the form of a plurality of staple fibers.

19. The fibers of claim 1, wherein the one or more ribulose-1,5-bisphosphate oxygenase protein fibers further comprise the plasticizer.

20. The fibers of claim 19, wherein the plasticizer comprises an alcohol, a polyalcohol, glycerol, gum arabic, or any combination thereof.

* * * * *